United States Patent [19]

Meggelaars et al.

[11] Patent Number: 5,534,555
[45] Date of Patent: Jul. 9, 1996

[54] TABLETING EXCIPIENT

[75] Inventors: Michael M. Meggelaars, Odiliapeel; Henricus A. van den Biggelaar; Klaas D. Kussendrager, both of Veghel, all of Netherlands

[73] Assignee: Campina Melkunie B.V., 's-Hertogenbosch, Netherlands

[21] Appl. No.: 262,344

[22] Filed: Jun. 20, 1994

Related U.S. Application Data

[63] Continuation of Ser. No. 868,712, Apr. 14, 1992, abandoned.

[30] Foreign Application Priority Data

Apr. 19, 1991 [NL] Netherlands ............................ 9100691

[51] Int. Cl.⁶ ....................................................... A61K 47/00
[52] U.S. Cl. .................................................................. 514/777
[58] Field of Search ............................. 426/658, 660; 514/53, 960, 777

[56] References Cited

U.S. PATENT DOCUMENTS 3,639,168  2/1972  Monti ........................................ 514/777
3,802,914  4/1974  Nezbed ...................................... 426/465
4,799,966  1/1989  Parrish et al. .
5,160,546  11/1992  Kawashima et al. ...................... 127/60

FOREIGN PATENT DOCUMENTS 1258549  1/1968  Germany .
2020982  11/1970  Germany .
1617638  5/1971  Germany .

OTHER PUBLICATIONS

Merck Index, 11th Ed, p. 843 Abst 5221, 1985.
Chem Abst. 109(25):229038, Dec. 19, 1988, Saito.
Derwent File Supplier WPI(L), 1981, AN=81-16266D.

*Primary Examiner*—Raymond Henley, III
*Attorney, Agent, or Firm*—Michael N. Meller

[57] ABSTRACT

A tableting excipient for making tablets by direct tableting in the form of a homogeneous mass consisting of a dried solution of lactose having a high β-lactose content, to which solution 1–15 wt. % of a sugar alcohol, calculated on the solids of the solution to be dried, has been added prior to drying.

9 Claims, 2 Drawing Sheets

TABLETING EXCIPIENT

This application is a continuation of application Ser. No. 07/868,712, filed Apr. 14, 1992 now abandoned.

This invention relates to a tableting excipient for manufacturing tablets by direct tableting.

Lactose products prepared by crystallization of lactose solutions consist almost entirely of lactose in the alpha form, particularly of α-lactose monohydrate. This ingredient is often used for manufacturing tablets, but this entails the necessity of a granulating treatment of a mixture of crystalline α-lactose monohydrate and active ingredients such as pharmacons, binders and disintegrants. This granulation comprises spraying with water or another solvent, whereby a part of the mixture dissolves and then functions as a binding agent between powder particles. Then the moisture is removed by drying, so that a granulate is formed that does not exhibit separation during the subsequent tableting treatment and hence can provide tablets of homogeneous quality.

Also because of the labour intensive character of a granulating treatment, there is a need for a tableting excipient which allows direct tableting.

Direct tableting or tableting by direct compression means that the mixture of ingredients to be compressed into a tablet is introduced into the dies of a tablet press as a powder mixture, without prior granulation, and is then formed into tablets under pressure by means of a punch.

In accordance with known proposals, lactose and other ingredients, such as sugar alcohols, are mixed dry or melted, whereafter the mixture thus obtained is used as an excipient for direct tableting.

German Offenlegungsschrift 1,617,638, for instance, discloses a method in which an excipient consisting of a mixture of 25% by weight of sorbitol and 75% of spray-dried lactose is mixed with a pharmacon and further adjuvants and processed into tablets without granulation. In view of the nature of the drying process for the lactose, this is present principally in the alpha form. Therefore, the tablet strength of tablets which are made using this excipient is not always satisfactory without granulating pretreatment.

U.S. Pat. No. 3,341,415 proposes as a tableting excipient a mixture of mannitol and lactose, without specifying how to prepare the lactose to be used.

U.S. Pat. '415 describes how lactose or other sugars are dissolved in molten mannitol and subsequently the congealed mixture of sugar and sugar alcohol can be used in the preparation of tablets by direct compression.

Although U.S. Pat. '415 includes a quantitative indication that the tablets so obtained exhibit a good tablet hardness, namely, up to 10 Strong-Cobb units, it appears in practice that such a hardness is not essentially greater than that of other tablets prepared with lactose, while, moreover, the production cost is substantially higher considering the price of mannitol.

It is known that tablets prepared by direct compression of a mixture containing an excipient comprising a substantial amount of β-lactose are qualitatively (particularly regarding firmness, capping and hardness) at least as good as tablets wherein the excipient consists of a mixture of lactose and sorbitol or mannitol.

U.S. Pat. No. 3,802,914, for instance, describes the preparation of a tableting excipient, in which lactose solutions comprising 40–60% by weight of solids are sprayed on the hot surface of a roll dryer, whereby a product is obtained that comprises at least 50 wt. % of amorphous lactose, because amorphous lactose generally consists of a mixture of α-lactose and β-lactose in a ratio of about 2:3, while the crystalline part of the product consists principally of β-lactose.

As is noted in the U.S. patent specification referred to, with respect to direct tableting, the excipient obtained must comprise a substantial amount (at least 50%) of lactose in amorphous form. However, a drawback thereof is that this amorphous lactose is not stable, since the ingredient has the tendency to attract moisture from the environment. In that case there is a risk of crystallization into α-lactose monohydrate. Such crystallization gives rise to the formation of lumps, while at the same time the advantages in direct tableting are lost.

Figure 1:
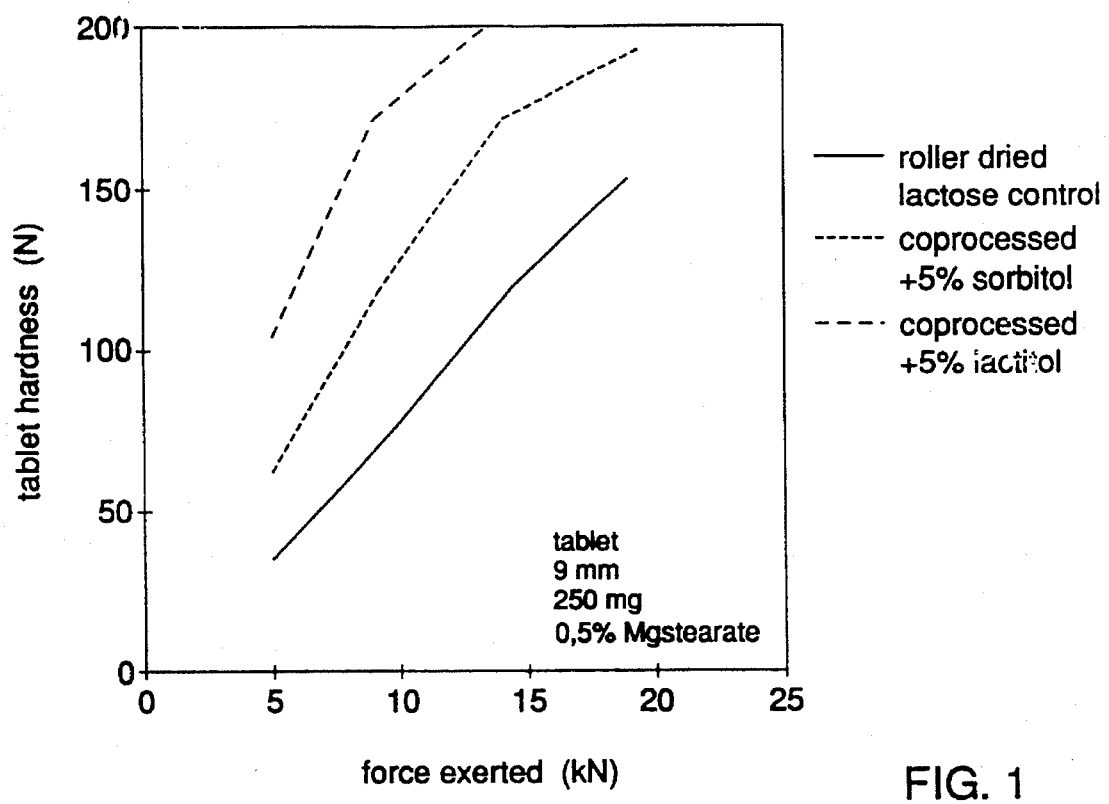
FIG. 1 shows the strengths of tablets prepared from compressed, roller dried solutions of lactose monohydrate alone, lactose monohydrate plus lactitol dihydrate and lactose monohydrate plus sorbitol.

According to the invention, it has been found that by means of direct tableting, tablets of an appreciably higher hardness than that of known tablets can be obtained when as a tableting excipient a dried solution of lactose of a high β-lactose content is employed, to which solution, prior to drying, 1–15% wt. % of a sugar alcohol, calculated on the solids of the solution to be dried, has been added.

Generally, products of good tableting properties are obtained from mixtures of lactose and sugar alcohols, obtained by roller drying a solution thereof according to the invention, particularly if use is made of mannitol, sorbitol, xylitol, lactitol, but also with mixtures of such alcohols, for instance obtained by hydrogenation of starch hydrolysates which comprise a mixture of mono-, di-, tri- and polysaccharides.

Very firm tablets are obtained in particular if use is made of lactitol, sorbitol or a mixture of these two sugar alchohols. When as little as 2 wt. % of lactitol or sorbitol is used, products are obtained that exhibit a clearly better behaviour in tableting than if lactose alone were used as a tableting excipient. If the sugar alcohol content exceeds 10 wt. %, the properties of such products become a little less favourable. If the sugar alcohol content exceeds 15 wt. %, a product can no longer be compared with conventional β-lactose products.

It has also been found that roller dried products of lactose with a sugar alcohol can exhibit particularly favourable tablet properties if the product also incorporates cellulose.

Although tablets which have been manufactured using a tableting excipient according to the invention already possess an excellent hardness and friability without the addition of cellulose, products which comprise both lactose and a sugar alcohol in combination with cellulose, if they have been prepared in accordance with the invention, even in combination with an appreciably higher content of a poorly tabletable active ingredient, such as paracetamol, can nevertheless yield firmer tablets than do products which, having the same ratio of adjuvant and active ingredient, do not comprise any cellulose. In particular, this concerns products which comprise up to 30 wt. % cellulose, not more than 5 wt. % water, between 50 and 99 wt. % lactose and between 1 and 15 wt. % lactitol and/or sorbitol.

The cellulose content may be raised according as more active ingredient is employed in addition to the excipient.

Dried solutions having a high β-lactose content, for instance a content in excess of 75%, can be obtained by methods which are known per se. It is important here (cfr. U.S. Pat. No. 3,802,914) that drying is done at a temperature above ca. 105° C. because then the water present is released from the product at a high temperature and the formation of β-lactose is promoted.

The preferred method of preparing products according to the invention is to dry on a roller dryer a homogeneous solution of lactose and sugar alcohol, in which, if so desired, the cellulose is suspended. Experience has taught that in such a case where the rolling temperature is sufficiently high, a product is obtained that consists principally of β-lactose in crystalline form.

For the preparation of the tableting excipient according to the invention, it is also possible to employ a co-extrusion of lactose and sugar alcohol, optionally together with a further adjuvant such as cellulose. This extrusion must be carried out carefully so as to avoid discoloration and decomposition, if any, of the sugar.

As noted, the excipient according to the invention, after conditioning at room temperature and at an air humidity of about 40%, has strikingly good tableting properties with no apparent lump formation or recrystallization into α-lactose hydrate through absorption of moisture. Excipients comprising substantial amounts of amorphous lactose, on the other hand, are partly converted to the hydrate form upon contact with humid air, so that the tableting properties deteriorate.

The firmness of a tablet is determined by first forming a tablet under standard conditions. Here, in addition to the dimensions and the weight of a tablet, the pressure at which the tablet is formed has an important influence on the firmness of the tablet obtained.

Then it is determined with an adapted testing device what force can be exerted on the tablet before it breaks under the load. By pressing a number of tablets and examining them one by one for crushing strength, a statistically reliable crushing strength value can be obtained.

In the same manner, it is possible to make tablets for a test. By shaking a number of tablets in a container for a given time according to a fixed pattern, it can be determined how much material has been abraded off the tablets. Expressed as a percentage of the total weight of the tablets examined, this rate is a measure of the friability.

Such a test can be performed with the product intended as a tableting excipient in unblended condition or with a particular amount of lubricant added, typically magnesium stearate. Although such a test generally gives a very important indication about the possibilities that can be realized with such an excipient if it is used in combination with active ingredients, such as medicaments, it is, of course, always important to determine whether the special advantages of a particular tableting excipient can actually be maintained if the excipient constitutes only a part of the ingredients of the tablet. In that case it is possible to examine the pressing of tablets as well as the crushing strength and friability per ingredient for mixtures of tableting excipient and active ingredient, with variations in content. In that case an eligible model active ingredient would for instance be paracetamol, which in pure form can hardly be compressed into tablets. The quality of a tablet having a high paracetamol content is therefore an important criterion for an assessment of the general qualities of the tableting excipient used.

The invention will be further illustrated and explained in and by the following Examples.

EXAMPLE 1

Three aqueous solutions were prepared, the first with lactose monohydrate, the second with lactose monohydrate plus lactitol dihydrate and the third with lactose monohydrate plus sorbitol. In all three solutions, the concentration was 60%. The solutions were dried by means of roller drying. Analysis of the products so obtained revealed that the lactose was present mainly as β-lactose.

The products obtained from the second and third solutions proved to contain 5% anhydrous lactitol and 5% sorbitol, respectively. Tablets were formed from the products so obtained by means of an eccentric press at increasing pressure. As a lubricant, magnesium stearate was used. The strength of the tablets so obtained was measured. The measuring results are shown in FIG. 1.

The tablet strength of the roller dried preparations comprising 5% sorbitol or lactitol was considerably higher than the tablet strength of the corresponding roller dried lactose.

EXAMPLE 2

Figure 2:
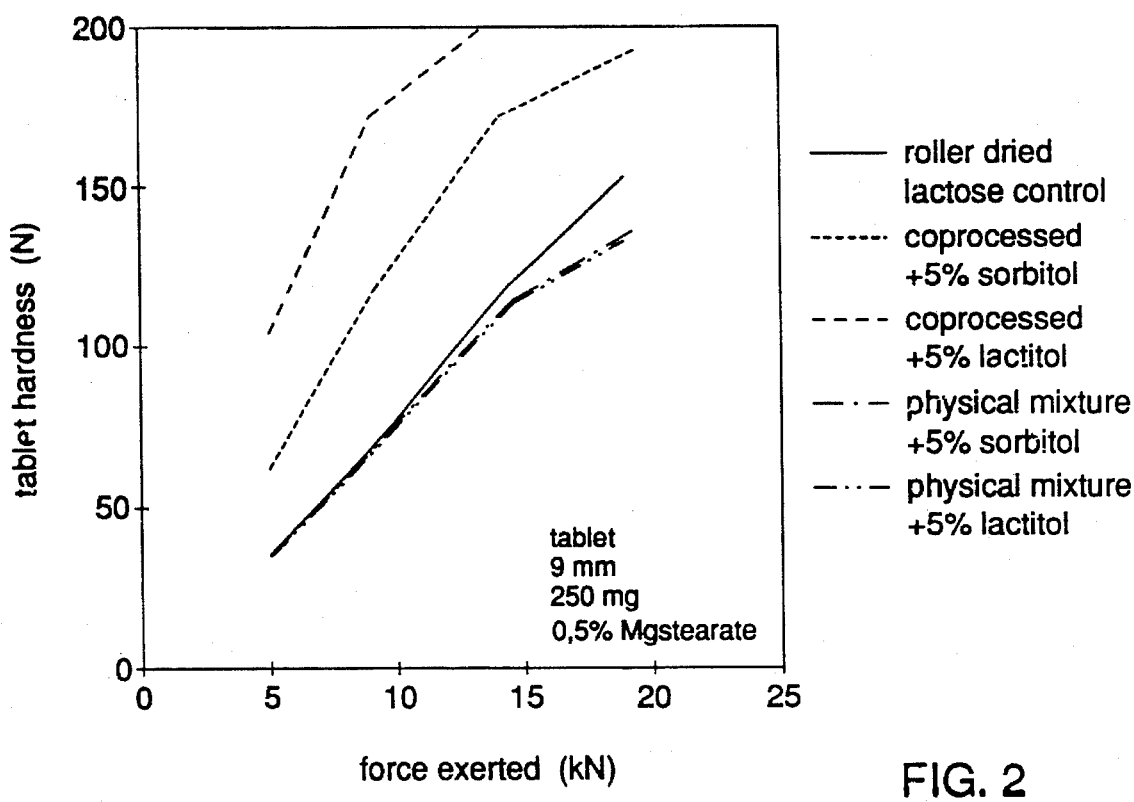
FIG. 2 shows the tablet strengths obtained in FIG. 1 and the strengths of tablets prepared from dry mixtures of lactose monohydrate plus lactitol dihydrate and lactose monohydrate plus sorbitol.

Dry mixtures of roller dried lactose (principally β-lactose) with 5% lactitol and 5% sorbitol, respectively, were prepared. From these dry mixtures, tablets were formed as described in Example 1. The tablet strengths were measured and compared with the tablet strengths of the products of Example 1. The measuring results are summarized in FIG. 2.

By dry addition of sorbitol or lactitol to roller dried lactose, the strength of the tablets obtained therefrom was not influenced, in contrast with the case where addition took place prior to roller drying.

EXAMPLE 3

Figure 3:
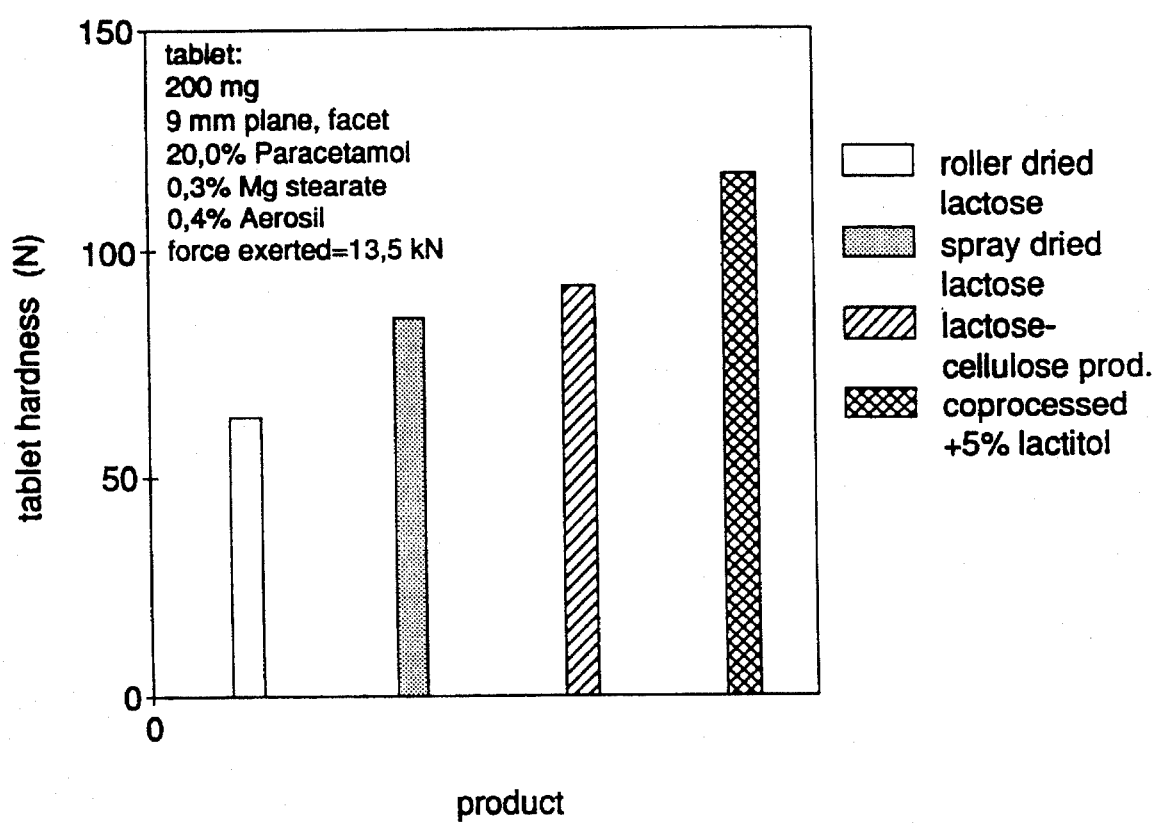
FIG. 3 shows the strength of tablets prepared from compressed roller dried lactose, spray dried lactose, a mixture of α-lactose and cellulose and the co-processed mixture of anhydrous lactose and lactitol dihydrate of FIG. 1. Each tablet also contains paracetamol, magnesium stearate and Aerosil.

The product obtained in Example 1, consisting of 95% anhydrous lactose with 5% lactitol, was mixed dry with 20% of the poorly compressible pharmacon (paracetamol) and tabletted after lubrication with magnesium stearate. Analogously, commercially available products for direct tableting (anhydrous roller dried lactose, spray dried lactose and a mixture of α-lactose and 30% cellulose) were tabletted after blending with 20% paracetamol and lubrication with magnesium stearate. All tablets were compressed at the same pressure. The tablets obtained were tested for tablet strength. The results are summarized in FIG. 3.

The product obtained by roller drying an aqueous solution of lactose and lactitol (95:5) exhibited a considerably higher tablet strength relative to commercially available products.

EXAMPLE 4

A mixture consisting of lactose monohydrate, lactitol dihydrate and cellulose was processed in an extruder with addition of water and at an elevated temperature, to form a product comprising 75% anhydrous lactose, mainly in the beta form, 5% anhydrous lactitol and 20% cellulose. This extruded preparation was mixed with different and increasing amounts of poorly compressible pharmacon (paracetamol) and after lubrication with magnesium stearate compressed into tablets on an eccentric press at a constant pressure. A similar series of tableting tests was performed with a commercially available anhydrous lactose (mainly in the beta form). The tablet strength of the tablets so obtained was measured. The Table below summarizes the measuring results.

TABLE

| Dose of paracetamol (%) | tablet strength in N | |
|---|---|---|
| | commercial product | extruded product |
| 0 | 81,2 | 149,4 |
| 20 | 63,9 | 106,2 |
| 30 | 27,3 * | 82,3 |
| 40 | * | 61,5 |
| 50 | * | 51,2 |
| 60 | * | 30,6 |

* tablets exhibit capping

The extruded product could incorporate about twice as much of the poorly compressible pharmacon (paracetamol) as the commercial product could, while sufficient tablet strength was maintained.

We claim:

1. An excipient for making tablets by direct tableting wherein said excipient is a homogeneous powdered solid composition comprising lactose which is predominantly β-lactose and 1–15 wt % of a sugar alcohol based on the amount of solids to be dried, said excipient obtained by drying a solution of lactose and sugar alcohol at a temperature sufficient to result in the lactose being predominantly in the β-lactose form.

2. A tableting excipient according to claim 1, wherein the lactose solution to be dried additionally contains cellulose in an amount between 5 and 40 wt. %, calculated on the solids in the solution to be dried.

3. A tableting excipient according to claim 2, wherein the sugar alcohol is mannitol, sorbitol, xylitol, lactitol, maltitol and/or a hydrogenated starch hydrolysate.

4. A tableting excipient according to claim 3, wherein the excipient contains 2–10 wt. % lactitol and 90–98 wt. % lactose, calculated on the solids content.

5. A tableting excipient according to claim 4, wherein the excipient contains 2–10 wt. % sorbitol and 90–98 wt. % lactose, calculated on the solids content.

6. A tableting excipient according to claim 2, which contains the following ingredients:

| Lactose, anhydrous | 40–99 wt. % |
|---|---|
| Lactitol, anhydrous | 1–15 wt. % |
| Cellulose | 0–40 wt. % |
| water | 0–5 wt. %. |

7. A tableting excipient according to claim 2, wherein the excipient contains the following ingredients:

| Lactose, anhydrous | 40–99 wt. % |
|---|---|
| Sorbitol, anhydrous | 1–15 wt. % |
| Cellulose | 0–40 wt. % |
| Water | 0–5 wt. %. |

8. A tablet comprising a compressed mixture of an excipient according to claim 1 and one or more active ingredients, chosen from a pharmacon, a sweetener, or a flavoring ingredient or mixtures thereof.

9. An excipient for making tablets by direct tableting, wherein said excipient is a homogeneous solid composition consisting of a dried solution of lactose and 1–15 wt % of a sugar alcohol based on the amount of solids to be dried, wherein the solution is dried at a temperature so that a solid composition is obtained which contains lactose which is predominantly β-lactose.

* * * * *